(12) United States Patent
Folan

(10) Patent No.: US 11,033,411 B2
(45) Date of Patent: Jun. 15, 2021

(54) STENT INCLUDING AN EXPANDABLE MEMBER

(71) Applicant: BOSTON SCIENTIFIC SCIMED, INC., Maple Grove, MN (US)

(72) Inventor: Martyn G. Folan, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 97 days.

(21) Appl. No.: 16/219,266

(22) Filed: Dec. 13, 2018

(65) Prior Publication Data

US 2019/0183666 A1 Jun. 20, 2019

Related U.S. Application Data

(60) Provisional application No. 62/598,747, filed on Dec. 14, 2017.

(51) Int. Cl.
*A61F 2/90* (2013.01)
*A61F 2/00* (2006.01)
(Continued)

(52) U.S. Cl.
CPC .............. *A61F 2/90* (2013.01); *A61F 2/0077* (2013.01); *A61F 2/848* (2013.01); *A61F 2/88* (2013.01); *A61F 2/92* (2013.01); *A61F 2/95* (2013.01); *A61F 2/07* (2013.01); *A61F 2/844* (2013.01); *A61F 2002/009* (2013.01); *A61F 2002/8486* (2013.01); *A61F 2002/9528* (2013.01); *A61F 2002/9534* (2013.01);
(Continued)

(58) Field of Classification Search
None
See application file for complete search history.

(56) References Cited

U.S. PATENT DOCUMENTS 5,693,088 A * 12/1997 Lazarus ................ A61F 2/07
606/195
6,264,689 B1 7/2001 Colgan et al.
(Continued)

FOREIGN PATENT DOCUMENTS

WO 2004049982 A2 6/2004
WO 2015195893 A1 12/2015

OTHER PUBLICATIONS

Davee et al., "Stent-in-stent Technique for Removal of Embedded Partially Covered Self-Expanding Metal Stents", Surg Endosc, 30: 2332-2341, 2016.
(Continued)

*Primary Examiner* — Leslie Lopez
(74) *Attorney, Agent, or Firm* — Seager, Tufte & Wickhem, LLP

(57) ABSTRACT

Example medical stents are disclosed. An example stent includes a tubular framework including an inner surface, an outer surface and a lumen extending therethrough. Additionally, the stent includes a tissue ingrowth scaffold extending along a portion of the outer surface of the tubular framework, wherein the tissue ingrowth scaffold is spaced radially away from the outer surface of the tubular framework to define an expansion cavity therebetween and wherein the tissue ingrowth scaffold permits tissue ingrowth along a portion thereof. Further, the stent includes an expandable member positioned within at least a portion of the expansion cavity.

19 Claims, 14 Drawing Sheets

(51) Int. Cl.
    *A61F 2/07*           (2013.01)
    *A61F 2/88*           (2006.01)
    *A61F 2/92*           (2013.01)
    *A61F 2/95*           (2013.01)
    *A61F 2/848*         (2013.01)
    *A61F 2/844*         (2013.01)

(52) U.S. Cl.
    CPC ............... *A61F 2210/0004* (2013.01); *A61F 2210/008* (2013.01); *A61F 2210/0061* (2013.01); *A61F 2230/001* (2013.01); *A61F 2240/001* (2013.01); *A61F 2250/0003* (2013.01); *A61F 2250/0039* (2013.01)

(56) References Cited

U.S. PATENT DOCUMENTS

| | | | |
|---|---|---|---|
| 6,283,992 | B1 | 9/2001 | Hankh et al. |
| 6,585,758 | B1 | 7/2003 | Chouinard et al. |
| 7,311,031 | B2 | 12/2007 | McCullagh et al. |
| 2002/0123789 | A1 | 9/2002 | Francis et al. |
| 2003/0149472 | A1 | 8/2003 | Pinchuk et al. |
| 2009/0210048 | A1* | 8/2009 | Amplatz .............. D04C 1/02 623/1.13 |
| 2011/0093058 | A1 | 4/2011 | Vardi |
| 2013/0073026 | A1* | 3/2013 | Russo .................. A61F 2/90 623/1.12 |
| 2013/0204351 | A1* | 8/2013 | Cox .................. A61B 17/12118 623/1.21 |
| 2014/0121759 | A1 | 5/2014 | Cully |
| 2014/0222039 | A1 | 8/2014 | Khrosrovaninejad |
| 2014/0350694 | A1 | 11/2014 | Behan |
| 2015/0045908 | A1 | 2/2015 | McMahon |
| 2015/0073544 | A1 | 3/2015 | Gorman, III et al. |
| 2016/0095724 | A1 | 4/2016 | Harris et al. |
| 2016/0296317 | A1 | 10/2016 | Timmermans et al. |
| 2018/0250118 | A1 | 9/2018 | Folan et al. |
| 2018/0280167 | A1 | 10/2018 | Folan et al. |

OTHER PUBLICATIONS

Hirdes et al., "Stent-in-Stent Technique for Removal of Embedded Esophageal Self-Expanding Metal Stents," Am J Gastroenterol 2011; 106:286-293.

Deviere et al., "Effectiveness of Endoscopic Management Using Self-Expandable Metal Stents in a Large Cohort of Patients with Post-bariatric Leaks," Obes Surg., 25: 1569-1576, 2015.

Eisendrath et al., "Endotherapy Including Temporary Stenting of Fistulas of the Upper Gastrointestinal TractAfter Laparoscopic Bariatric Surgery," Endoscopy, 39: 625-630, 2007.

International Search report and Written Opinion dated May 29, 2018 for International Application No. PCT/US2018/020474, 11 pages.

International Search Report and Written Opinion dated Jun. 18, 2018 for International Application No. PCT/US2018/024456, 13 pages.

Water Gel Crystals Expanding Polymers—snow polymers, http://watergelcrystals.com/snow.htm, Mar. 13, 2019 (5 pages).

* cited by examiner

STENT INCLUDING AN EXPANDABLE MEMBER

CROSS-REFERENCE TO RELATED APPLICATIONS

This application claims priority under 35 U.S.C. § 119 to U.S. Provisional Application Ser. No. 62/598,747, filed Dec. 14, 2017, the entirety of which is incorporated herein by reference.

TECHNICAL FIELD

The present disclosure pertains to medical devices, methods for manufacturing medical devices, and the use thereof. More particularly, the present disclosure pertains to stents designed to be removed from the body and methods for manufacturing and using such stents.

BACKGROUND

A wide variety of intracorporeal medical devices have been developed for medical use, for example, intravascular use. In some instances the medical devices (e.g., self-expanding stents) are placed in a body lumen (e.g., esophagus, gastrointestinal tract, etc.) for the treatment of a variety of disorders. However, in some instances the compressible and flexible properties that assist in stent positioning may also result in a stent that has a tendency to migrate from its originally deployed position. For example, stents that are designed to be positioned in the esophageal or gastrointestinal tract may have a tendency to migrate due to peristalsis (i.e., the involuntary constriction and relaxation of the muscles of the esophagus, intestine, and colon which push the contents of the canal therethrough). Additionally, the generally moist and inherently lubricious environment of the esophagus, intestine, colon, etc. further contributes to a stent's tendency to migrate when deployed therein. One method to reduce stent migration may include exposing bare portions of the stent to the tissue of the body lumen. The stent scaffold may provide a structure that promotes tissue ingrowth into the interstices or openings thereof (e.g., the stent structure may promote a hyperplastic response). The tissue ingrowth may anchor the stent in place and reduce the risk of stent migration.

Additionally, while it is important to design stents that reduce the degree to which a stent migrates within a body lumen, it is also important to design stents that may be easily removed and/or re-positioned from the body lumen post-deployment. Stents including bare portions (i.e., uncovered portions) designed to promote tissue ingrowth (e.g., to reduce stent migration as described above) may consequently be more difficult to remove once the tissue has anchored the stent in the body lumen.

BRIEF SUMMARY

This disclosure provides design, material, manufacturing method, and use alternatives for medical devices. An example stent includes a tubular framework including an inner surface, an outer surface and a lumen extending therethrough. Additionally, the stent includes a tissue ingrowth scaffold extending along a portion of the outer surface of the tubular framework, wherein the tissue ingrowth scaffold is spaced radially away from the outer surface of the tubular framework to define an expansion cavity therebetween and wherein the tissue ingrowth scaffold permits tissue ingrowth along a portion thereof. Further, the stent includes an expandable member positioned within at least a portion of the expansion cavity.

Alternatively or additionally to any of the embodiments above, wherein the expandable member is configured to expand radially outward toward an inner surface of the tissue ingrowth scaffold.

Alternatively or additionally to any of the embodiments above, wherein the expandable member is configured to exert a radially outward expansion force on the tissue ingrowth scaffold such that the outer surface of the tissue ingrowth scaffold shifts radially outward from a first positon to a second position.

Alternatively or additionally to any of the embodiments above, wherein the expandable member is configured to exert a radially outward force upon the tissue ingrowth scaffold causing tissue ingrowth to recede.

Alternatively or additionally to any of the embodiments above, wherein the expandable member extends circumferentially around the outer surface of the tubular framework.

Alternatively or additionally to any of the embodiments above, wherein the expandable member includes an expandable sleeve and an expandable material positioned within a void of the expandable sleeve.

Alternatively or additionally to any of the embodiments above, wherein the expandable material is configured to expand when exposed to an external stimuli.

Alternatively or additionally to any of the embodiments above, wherein the external stimuli is a liquid.

Alternatively or additionally to any of the embodiments above, wherein the expandable sleeve is configured to dissolve over a time period to expose the expandable material.

Alternatively or additionally to any of the embodiments above, wherein the expandable member includes an inflatable sleeve, and wherein the inflatable sleeve is configured to shift from a first unexpanded configuration to a second expanded configuration when inflated.

Alternatively or additionally to any of the embodiments above, wherein the tissue ingrowth scaffold extends along the outer surface of the tubular framework from an end of the tubular framework, and wherein the scaffold folds back on the tubular framework to form the expansion cavity.

Alternatively or additionally to any of the embodiments above, further comprising a covering disposed along a portion of the tubular framework, wherein the covering is configured to prevent tissue from growing into the lumen of the tubular framework.

Alternatively or additionally to any of the embodiments above, wherein the tissue ingrowth scaffold includes a wire mesh having one or more apertures configured to permit tissue ingrowth therethrough.

Another example stent includes a tubular framework having a first end and a second end opposite the first end. The tubular framework includes an inner surface, an outer surface and a lumen extending therethrough. A tissue ingrowth scaffold extends along a portion of the outer surface of the tubular framework. The tissue ingrowth scaffold is spaced radially away from the outer surface of the tubular framework to define an expansion cavity therebetween. The tissue ingrowth scaffold permits tissue ingrowth along a portion thereof. A covering is disposed along the tubular framework. The covering is configured to prevent tissue from growing into the lumen of the tubular framework between the first end and the second end. An expandable member is positioned within at least a portion of the expansion cavity. The expandable member is configured to radially expand from a first nominal state to an expanded state when subjected to an external stimuli. The expandable member is configured to exert a radially outward force upon the tissue ingrowth scaffold in the expanded state to cause tissue ingrowth within the tissue ingrowth scaffold to recede.

Alternatively or additionally to any of the embodiments above, wherein the expandable member is configured to expand radially outward toward an inner surface of the tissue ingrowth scaffold.

Alternatively or additionally to any of the embodiments above, wherein the expandable member extends circumferentially around the outer surface of the tubular framework.

Alternatively or additionally to any of the embodiments above, wherein the expandable member includes an expandable sleeve and an expandable material positioned within a void of the expandable sleeve.

Alternatively or additionally to any of the embodiments above, wherein the external stimuli is a liquid.

Alternatively or additionally to any of the embodiments above, wherein the expandable sleeve is configured to dissolve over a time period to expose the expandable material.

Alternatively or additionally to any of the embodiments above, wherein the tissue ingrowth scaffold includes a wire mesh having one or more apertures configured to permit tissue ingrowth therethrough.

An example method of treating a body lumen includes activating an expandable member positioned between a tissue ingrowth scaffold and a tubular framework of a pre-deployed stent having tissue ingrown into the tissue ingrowth scaffold. Activating the expandable member causes the expandable member to shift radially from a first unexpanded configuration to a second expanded configuration. Shifting the expandable member from a first unexpanded configuration to a second expanded configuration includes exerting a radially outward force upon the tissue which has grown into the tissue ingrowth scaffold. Exerting a radially outward force upon the tissue which has grown into the tissue ingrowth scaffold causes the tissue to recede.

The above summary of some embodiments is not intended to describe each disclosed embodiment or every implementation of the present disclosure. The Figures and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
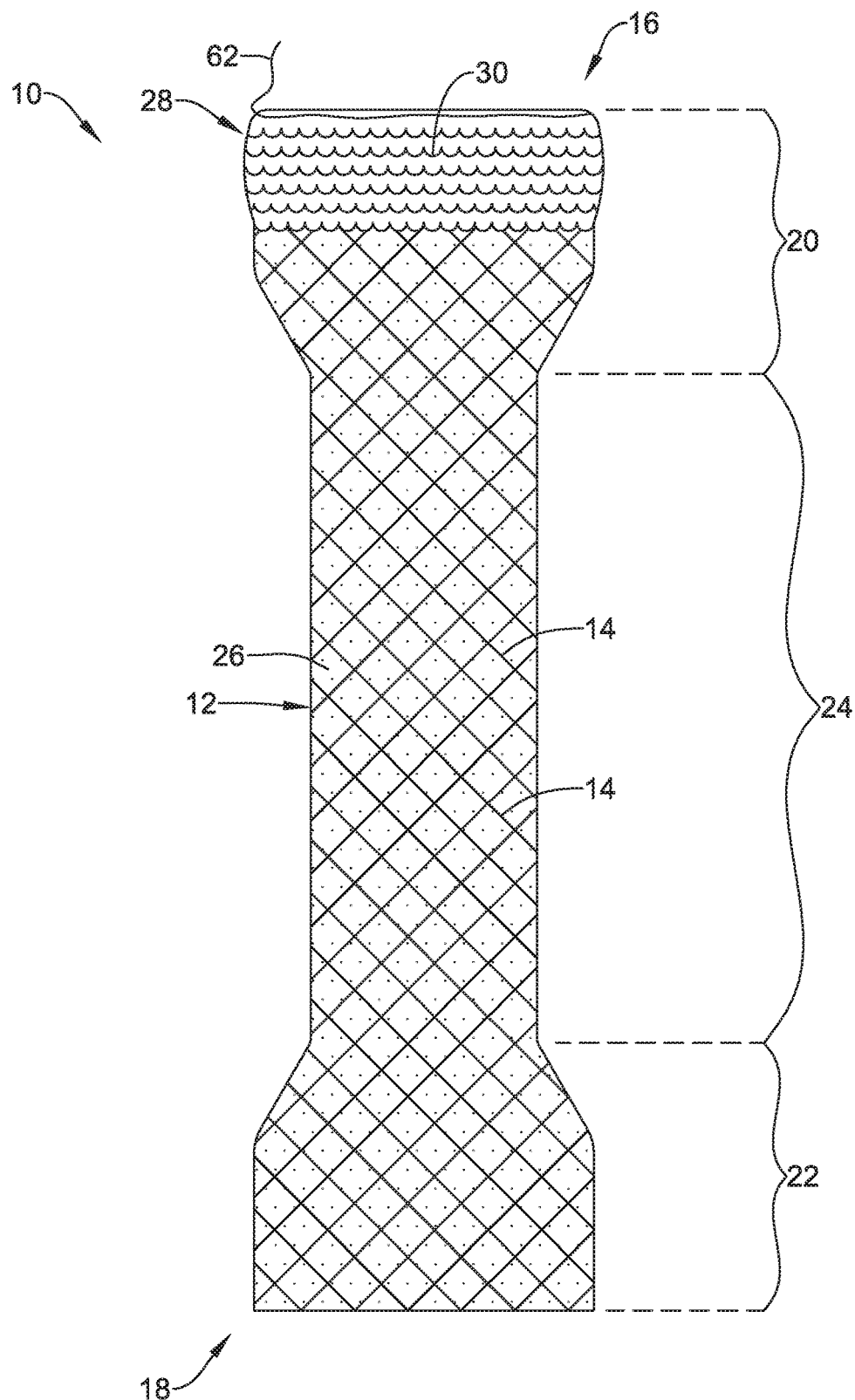
FIG. 1 is a side view of an example stent.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

As discussed above, in some instances an implantable medical device may be designed to provide a pathway for digested material, blood, or other fluid to flow therethrough following a medical procedure. These medical devices may include radially or self-expanding stents which may be implanted transluminally via an endoscope or similar medical device. Additionally, some stents may be implanted in a variety of body lumens such as the esophageal tract, the gastrointestinal tract (including the intestine, stomach and the colon), tracheobronchial tract, urinary tract, biliary tract, vascular system, etc.

In some instances it may be desirable to design a stent which includes sufficient radial strength to maintain its positon within a body lumen while also having the ability to function as a passageway for food or other digested material to flow therethrough. However, in some stents, the compressible and flexible properties that assist in stent positioning may also result in a stent that has a tendency to migrate from its originally deployed position. For example, stents that are designed to be positioned in the esophageal or gastrointestinal tract may have a tendency to migrate due to peristalsis (i.e., the involuntary constriction and relaxation of the muscles of the esophagus, intestine, and colon which push the contents of the canal therethrough). Additionally, the generally moist and inherently lubricious environment of the esophagus, intestine, colon, etc. further contributes to a stent's tendency to migrate when deployed therein. One method to reduce stent migration may include exposing bare metal portions of the stent to the tissue of the body lumen. The stent scaffold may provide a structure that promotes tissue ingrowth (e.g., a hyperplastic response) into the interstices or openings thereof. The tissue ingrowth may anchor the stent in place and reduce the risk of stent migration.

Additionally, while it is important to design stents that reduce the degree to which a stent migrates within a body lumen, it is also important to design stents that may be easily removed and/or re-positioned from the body lumen post-deployment. Stents including bare portions (i.e., uncovered portions) designed to promote tissue ingrowth (e.g., to reduce stent migration as described above) may consequently be more difficult to remove once the tissue has anchored the stent in the body lumen. Thus, it may be desirable to provide a stent that permits tissue ingrowth to inhibit stent migration, while also permitting less traumatic selective removability of the stent. One method to reduce the force and/or tissue trauma necessary to remove a stent from a body lumen, as disclosed herein, may include expanding an expandable member radially outward against the ingrown tissue. The radial expansion of the expandable member may cause the tissue ingrowth to recede, thereby reducing the force and/or tissue trauma necessary to remove the stent from the wall of the body lumen. Examples of stents including a radially expandable member are disclosed herein.

FIG. 1 shows an example stent 10. The stent 10 may include a tubular framework 12 having a first end 16, which may extend to the first end of the stent 10, a second end 18, which may extend to the second end of the stent 10, and a lumen extending therethrough. When positioned in a body lumen (e.g., esophagus) the first or proximal end 16 may be defined as the end of stent 10 closest to a patient's mouth and the second or distal end 18 may be defined as the end of the stent 10 closest to a patient's stomach.

The tubular framework 12 may be configured to provide the support structure for the stent 10. The tubular framework 12 may be formed of one or more stent filaments 14, or a plurality of stent filaments 14. The filaments 14 may extend longitudinally along the stent 10. In some instances, the filaments 14 may extend longitudinally along the stent 10 in a helical fashion. While FIG. 1 shows the filaments 14 extending along the entire length of the stent 10 between the first end 16 and the second end 18 of the stent 10, in other examples, the filaments 14 may extend only along a portion of the length of stent 10. Further, FIG. 1 shows that stent 10 may include a retrieval suture 62 extending circumferentially around the first end 16 of the stent 10. Retrieval suture 62 may be looped through the filaments 14, for example.

Additionally, FIG. 1 shows the example stent 10 including a first flared end region 20 proximate the first end 16 and/or a second flared region 22 proximate the second end 18 of the stent 10. In some instances, the first flared region 20 and the second flared region 22 may be defined as an increase in the outer diameter, the inner diameter or both the inner and outer diameter along one or both of the first end 16 and/or the second end 18 of the stent 10 relative to an outer diameter of a medial region 24 of the stent 10 therebetween. Further, FIG. 1 illustrates the stent 10 including a medial region 24 having a cylindrical configuration positioned between the first flared region 20 and the second flared region 22.

However, it is contemplated that while FIG. 1 shows the stent 10 including both a first flared region 20 and a second flared region 22, the stent 10 may only include one flared region. For example, it is contemplated that the stent 10 may include only the first flared region 20 or the second flared region 22, or the stent 10 may have a constant diameter along its entire length. It is further contemplated that all or a portion of the first flared region 20 and/or the second flared region 22 may flare outwardly (e.g., away from the central, longitudinal axis of stent 10). Alternatively, it is further contemplated that all or a portion of the first flared region 20 and/or the second flared region 22 may flare inwardly (e.g., toward the central, longitudinal axis of stent 10).

In some instances, the stent 10 may be a self-expanding stent. Self-expanding stent examples may include stents having one or more interwoven filaments 14 to form the tubular framework 12, having openings defined between adjacent filaments 14. For example, the stent filaments 14 may be wires braided, knitted or otherwise interwoven to form the tubular framework 12. Openings or interstices through the wall of the tubular framework 12 may be defined between adjacent stent filaments 14. Alternatively, the tubular framework 12 of the stent 10 may be a monolithic structure formed from a cylindrical tubular member, such as a single, cylindrical tubular laser-cut Nitinol tubular member, in which the remaining portions of the tubular member form the stent filaments 14 with openings defined therebetween.

The stent 10, or components thereof, (including the tubular framework 12 and/or the stent filaments 14) disclosed herein may be constructed from a variety of materials. For example, the stent 10 (e.g., self-expanding or balloon expandable), or components thereof, may be constructed from a metal (e.g., Nitinol). In other instances, the stent 10 or components thereof may be constructed from a polymeric material (e.g., PET). In yet other instances, the stent 10, or components thereof, may be constructed from a combination of metallic and polymeric materials. Additionally, the stent 10, or components thereof, may include a bioabsorbable and/or biodegradable material.

Figure 2:
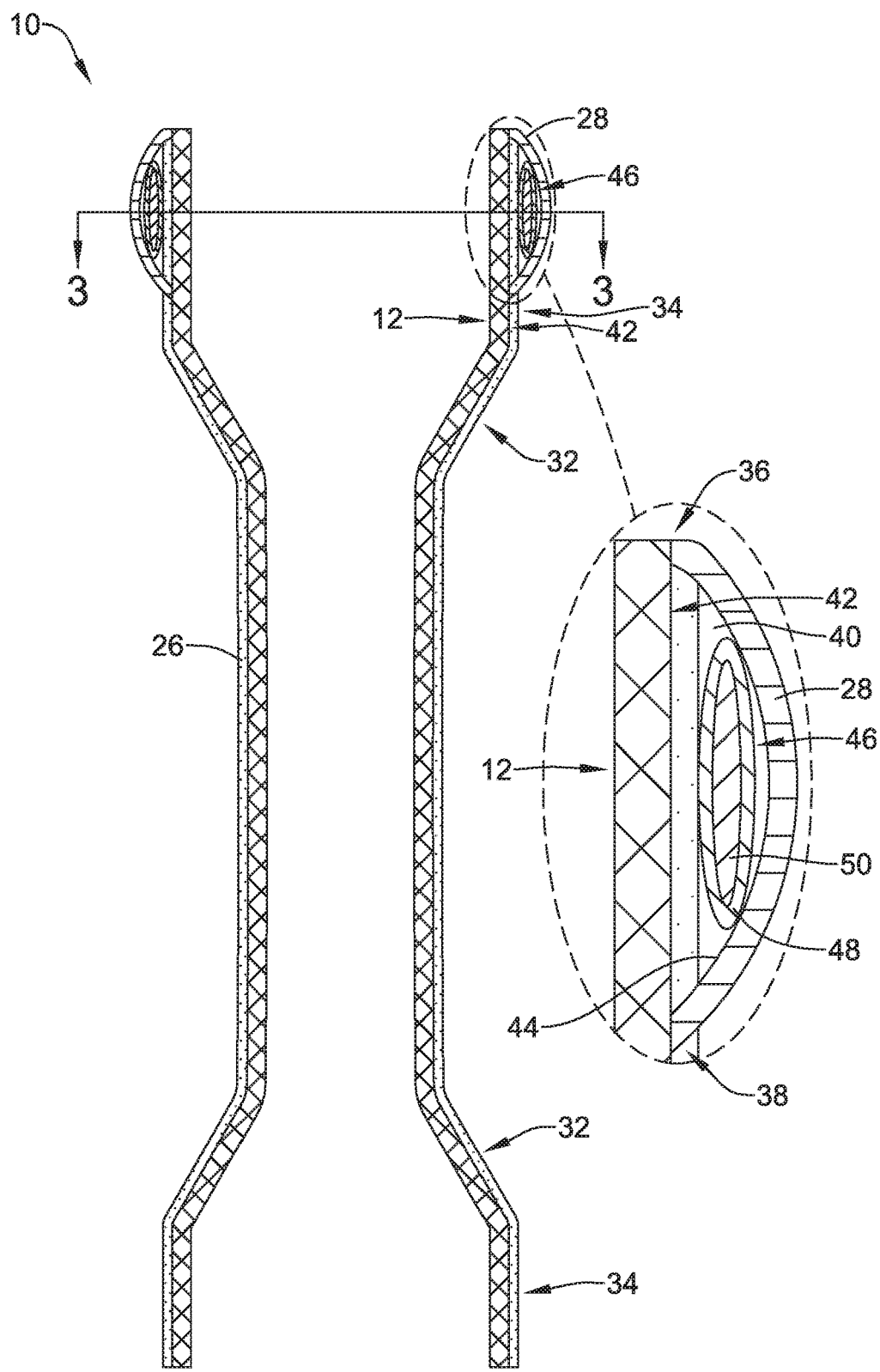
FIG. 2 is a cross-sectional view of the stent shown in FIG. 1.

Additionally, the stent 10 may include one or more covering layers 26 disposed on the tubular framework 12, such as positioned on and/or adjacent to the inner surface and/or outer surface thereof. The covering layer 26 may be positioned on a portion of the filaments 14 forming the tubular framework 12 and extend across openings or cells between adjacent filaments 14. For example, FIG. 2 shows the stent 10 including a covering layer 26 disposed along the outer surface of the tubular framework 12. In some instances, the covering layer 26 may be an elastomeric or non-elastomeric material. For example, the covering layer 26 may be a polymeric material, such as silicone, polyurethane, or the like. Further, the covering layer 26 may span the spaces (e.g., openings, cells, interstices) in the wall of the tubular framework 12 defined between adjacent filaments 14. For example, the covering layer 26 may extend along and cover the inner surface and/or outer surface of the tubular framework 12 such that the covering layer 26 spans one or more spaces (e.g., openings, cells, interstices) between the filaments 14 in the wall of the tubular framework 12. In some instances, the covering layer 26 may extend circumferentially around the entire circumference of the tubular framework 12 and extend the entire length of the tubular framework 12 from the first end 16 to the second end 18 such that the covering layer 26 covers each opening or interstice of the tubular framework 12, thus forming a completely covered stent to prevent tissue ingrowth into the lumen of the stent 10.

As described above, the stent 10 may have a first end 16 and a second end 18. When positioned in a body lumen, the first end 16 may be defined as the proximal end of the stent 10 and oriented as the end of the stent 10 closest to a patient's mouth and second end 18 may be defined as the distal end of stent 10 and oriented as the end of stent 10 closest to a patient's stomach. As shown in FIG. 2, the covering layer 26 may extend along the length of the tubular framework 12 from the first end 16 to the second end 18. In other words, in some instances the covering layer 26 may be defined as a continuous layer that extends from first end 16 to second end 18 of stent 10 and fully extends across and fills cells or interstices defined between filaments 14 of the tubular framework 12. However, in other instances covering layer 26 may extend less than the entire length of stent 10, if desired, leaving a portion of cells or interstices defined between the filaments 14 of the tubular framework 12 unfilled or open.

FIG. 1 further illustrates that in some examples, the stent 10 may include a tissue ingrowth scaffold 28 extending along a portion of the outer surface of the tubular framework 12. The tissue ingrowth scaffold 28 may be defined as an uncovered region (e.g., a tissue ingrowth-promoting section, an anti-migration section, etc.) of the stent 10. The uncovered openings present in the tissue ingrowth scaffold 28 may permit the stent 10 to be securely implanted (e.g., permit tissue ingrowth) at a target site (e.g., within a body lumen). As will be described in further detail below, the tissue ingrowth scaffold 28 may include wires 30 that are braided, knitted or otherwise interwoven together to form the tissue ingrowth scaffold 28. In some examples, the tissue ingrowth scaffold 28 may be free from the covering 26 described above. For example, the covering 26 may extend radially within the tissue ingrowth scaffold 28 but be unattached to or otherwise not obstruct tissue ingrowth into the tissue ingrowth scaffold.

FIG. 2 shows a cross-section of the example stent 10 of FIG. 1. FIG. 2 illustrates that the first flared region 20 and/or the second flared region 22 of stent 10 may include tapered portions 32 and end portions 34. While FIG. 2 shows the tapered portions 32 tapering radially outward toward ends of stent 10, it is contemplated that one or more of the tapered portions 32 may, alternatively, taper radially inward.

As described above, the stent 10 may include the tissue ingrowth scaffold 28 extending along an outer surface 42 of the tubular framework 12, radially outward of the covering layer 26. The tissue ingrowth scaffold 28 may be located at any desired location along the tubular framework 12. For example, a first end of the tissue ingrowth scaffold 28 may be coupled (e.g., attached) to the outer surface 42 of the tubular framework 12 at an end point 36 of the end portion 34 of the first end 16 of the stent 10. A second end of the tissue ingrowth scaffold 28 may be coupled (e.g., attached) to the outer surface 42 of the tubular framework 12 at a connection point 38 along the end portion 34 of the first end 16 of the stent 10. Various attachment techniques may be utilized to attach the tissue ingrowth scaffold 28 to the tubular framework 12. For example, the tissue ingrowth scaffold 28 may be attached via welding, suturing, stitching, etc. Additionally, while FIG. 2 shows the connection point 38 being positioned along the end portion 34, it is contemplated that the connection point 38 may be positioned along tapered region 32, for example.

The detailed view of FIG. 2 illustrates the tissue ingrowth scaffold 28 attached at both the end point 36 and the connection point 38, as described above. Further, it can be appreciated that the tissue ingrowth scaffold 28, along with the tubular framework 12, may form an expansion "cavity" 40 bounded by the outer surface 42 of the tubular framework 12 and the inner surface 44 of the tissue ingrowth scaffold 28. The expansion cavity 40 may define a void, or space, which is bounded by the outer surface 42 of the tubular framework 12 and the inner surface 44 of the tissue ingrowth scaffold 28. As will be described in greater detail below, the tissue ingrowth scaffold 28 may extend circumferentially around the outer surface 42 of the tubular framework 12. Therefore, it can be appreciated that the expansion cavity 40 may entirely extend circumferentially around the outer surface of the tubular framework 12 of the stent 10 in some instances.

FIG. 2 further illustrates that in some examples, stent 10 may include an expansion member 46 positioned within the expansion cavity 40. In some examples, the expansion member 46 may entirely extend circumferentially around the outer surface 42 of the tubular framework 12. As will be described in greater detail below, the expansion member 46 may expand from a first unexpanded configuration to a second expanded configuration. In the expanded configuration, the expansion member 46 may conform and fill the space defined by the expansion cavity 40. In other examples, the expansion member 46 may expand to alter the shape of the expansion cavity 40 by exerting a radial outward force upon the tissue ingrowth scaffold 28.

As illustrated in the detailed view of FIG. 2, the expansion member 46 may include an expandable material 50 surrounded by an outer sleeve 48 in some instances. The outer sleeve 48 may be constructed from polymeric material which permits the sleeve 48 to stretch, expand and/or change shape as needed. It can be appreciated that sleeve 48 may be shaped like a torus. Example materials that may be utilized to construct the sleeve 48 may include silicone, Chronoflex®, UE, PVDF, PTFE or other similar materials. Further, as will be discussed in greater detail below, it is contemplated that the sleeve 48 may be constructed from a biodegradable material in some instances. The biodegradable material may be designed to degrade over a specific time period to expose the expandable material 50 within the outer sleeve 48. For example, the sleeve 48 may be constructed from a biodegradable material that biodegrades upon exposure to magnetic waves, an electromagnetic field (EMF), electrical signals, various liquids, heat, etc. A non-limiting list of materials which may be utilized to construct sleeve 48 are disclosed below.

A variety of different materials are contemplated for the expandable material 50. For example, the expandable material 50 may include a superabsorbent material, superabsorbent polymer (e.g., superabsorbent water absorbing crystal polymers including, but not limited to crosslinked polyacrylic acid), superabsorbent polymer composites, electroactive polymers and/or other similar materials. A common, beneficial property of these materials is that they may expand from a first volume to a second volume when contacted by a particular media. For example, these materials may expand when contacted by a liquid or aqueous solution such as water, DI water, saline, urine, blood, etc.

While FIG. 2 illustrates the tissue ingrowth scaffold 28 disposed along the distal portion 34 of the tubular framework 12, it is contemplated that the tissue ingrowth scaffold 28 may be positioned at any point along the outer surface 42 of the tubular framework 12. For example, the tissue ingrowth scaffold 28 may be positioned along the tapered regions 32 and/or the medial region 24 of the stent 10. Further, it is contemplated that the stent 10 may include more than one tissue ingrowth scaffold 28. For example, the stent 10 may include a combination of tubular scaffolds 28 positioned along the first flared region 20, the second flared region 22 and/or the medial region 24.

Figure 3:
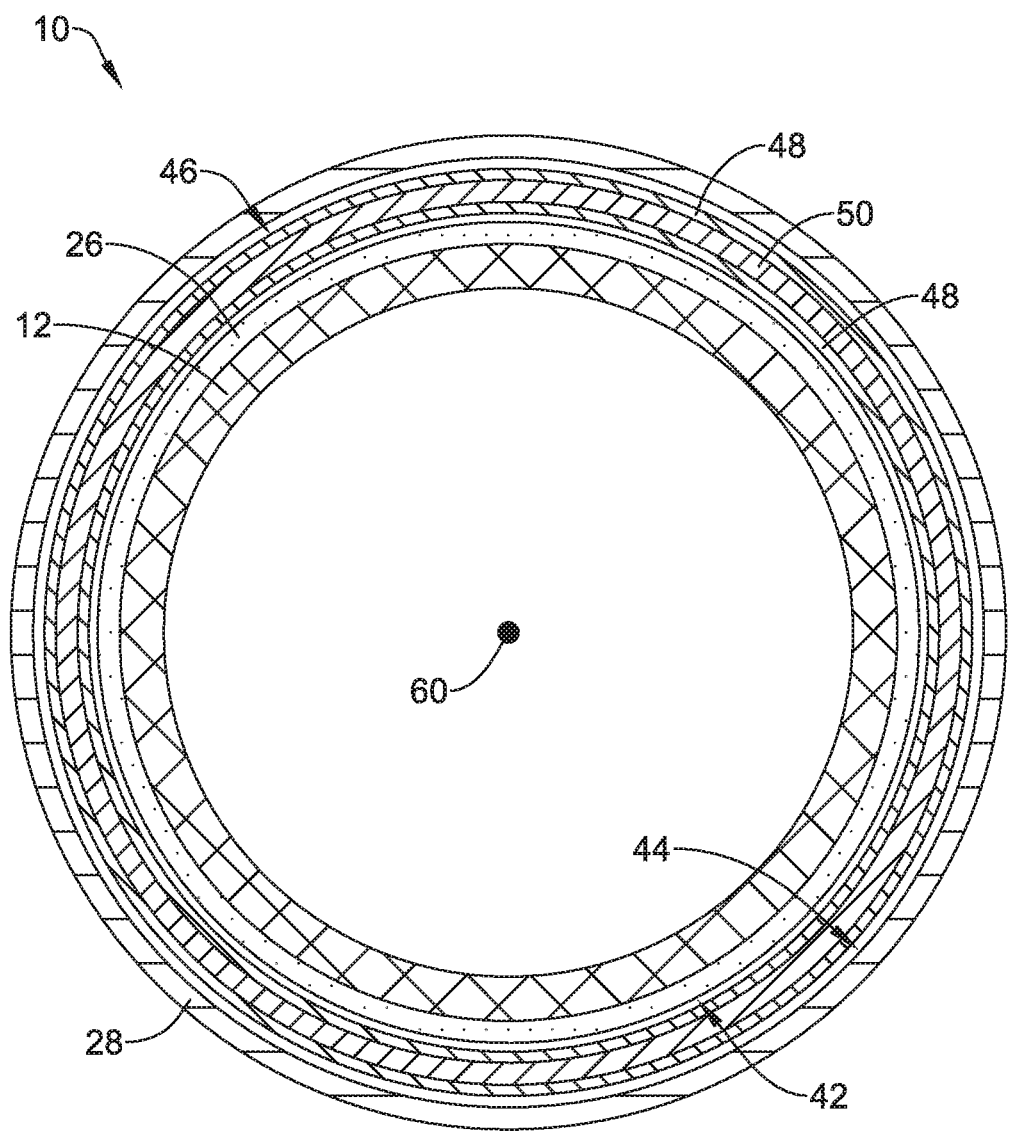
FIG. 3 is a cross-sectional view along line 3-3 of the stent shown in FIG. 2.

FIG. 3 shows a cross-sectional view of the stent 10 taken along line 3-3 of FIG. 2. FIG. 3 shows tubular framework 12 extending circumferentially around the longitudinal axis 60 of the stent 10. Additionally, covering 26, such as a polymeric coating, is shown disposed along the tubular framework 12. Further, FIG. 3 illustrates the expandable member 46 positioned between the outer surface 42 of the tubular framework 12 and the inner surface of the tissue ingrowth scaffold 28. FIG. 3 further illustrates the expandable material 50 positioned within an expandable sleeve 48 of the expandable member 46.

Figure 4:
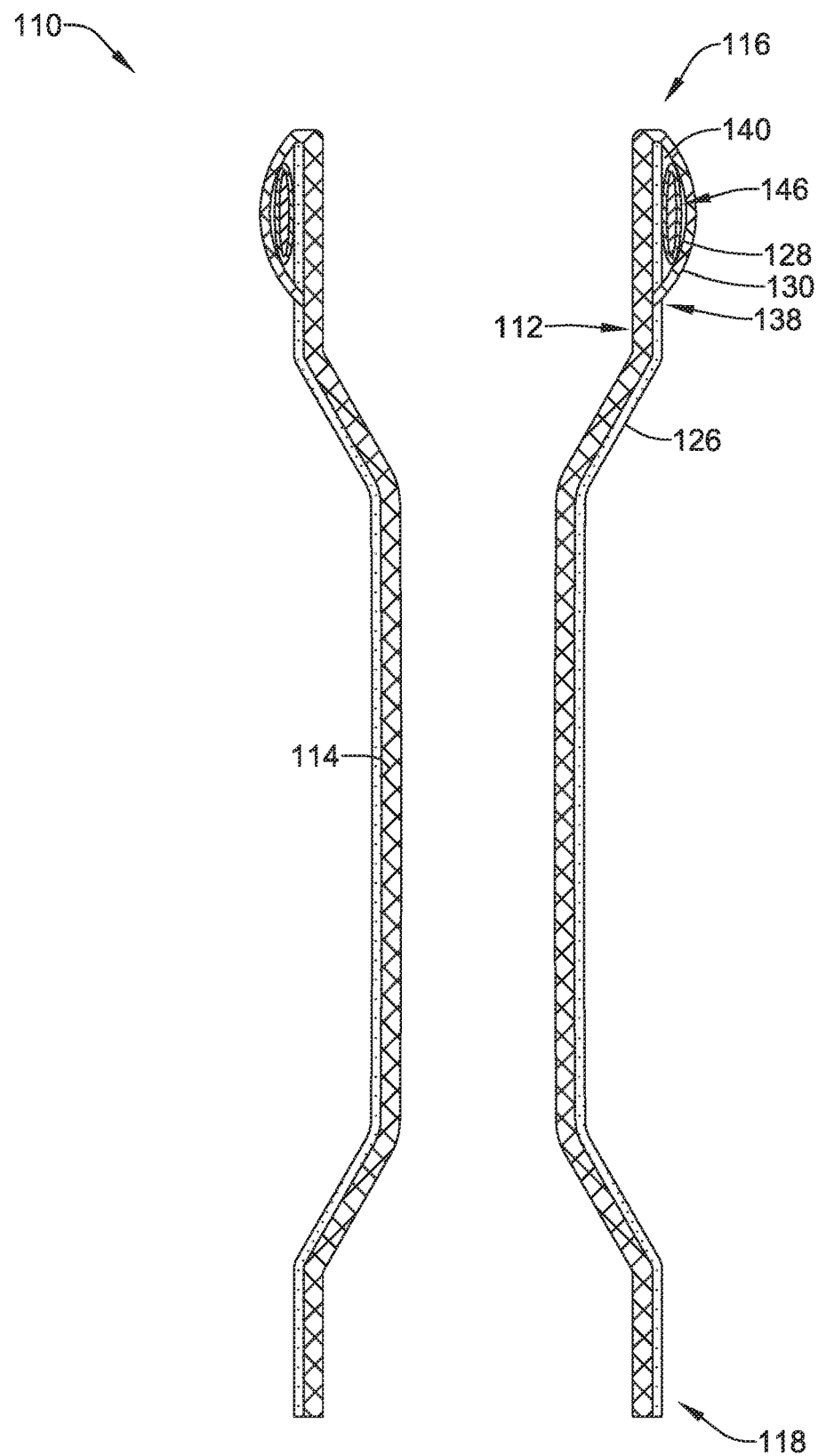
FIG. 4 is a cross-sectional view of another example stent.

FIG. 4 illustrates another example stent 110. Example stent 110 may be similar in form and function to the example stent 10 described above. For example, the stent 110 may include a tubular framework 112 having a covering 126 disposed along a portion thereof. The tubular framework 112 may be constructed from wires and/or filaments 114. Further, the stent 110 may include a tissue ingrowth scaffold 128 extending along a portion of the outer surface of the tubular framework 112, radially outward of the covering 126. The tissue ingrowth scaffold 128 may include wires and/or filaments 130 which are braided, knitted, etc. to form an expandable scaffold designed to promote tissue to grow thereon.

Additionally, FIG. 4 further illustrates that the tissue scaffold 128 may be formed from the wires and/or filaments 114 used to construct the tubular framework 112. For example, FIG. 4 shows that the tissue ingrowth scaffold 128 may be formed as an extension of the wires and/or filaments 114 of tubular framework 112 which are folded back on the tubular framework 112 and attached to the outer surface of the tubular framework 112 (at attachment point 138, for example). Thus, the tissue ingrowth scaffold 128 may be constructed of wires and/or filaments 114 of the tubular framework 112 folded back at the first end 116 and extending toward the second end 118 radially outward of the tubular framework 112. In other examples, the wires and/or filaments 130 used to construct the tissue ingrowth scaffold 128 may be different from the wires and/or filaments 114 used to construct the tubular scaffold 112, yet they may be interwoven with each other.

It can be appreciated from FIG. 4 that the tissue ingrowth scaffold 128 and the tubular framework 112 may form an expansion cavity 140 therebetween which is similar in form and function to the expansion cavity 40 discussed above. It can be further appreciated that the stent 110 may include an expandable member 146 positioned within the expansion cavity 140. The expandable member 146 may be similar in form and function to the expandable member 46 discussed above.

As discussed above, stents that are designed to be positioned in a body lumen (e.g., esophageal or gastrointestinal tract) may have a tendency to migrate (due to peristalsis and/or the generally moist and inherently lubricious environment of the body lumens). Therefore, one method to reduce stent migration may include exposing tissue ingrowth promoting regions, such as uncovered and/or bare metal portions of the stent to the tissue of the body lumen. The uncovered or bare stent scaffold may provide a structure that promotes tissue ingrowth into the interstices or openings thereof. The tissue ingrowth may anchor the stent in place and reduce the risk of stent migration.

Accordingly, it can be appreciated that the portions of the stent 10 discussed above which include the covering 26 which covers the stent struts or filaments 14 may act to prevent tissue from growing into the interstices or openings thereof, and thus prevent tissue ingrowth into the lumen of the stent. For example, the struts or filaments 14 of the end portions 34, tapered regions 32 and medial region 24 of the stent 10 which includes the covering 26 attached thereto to thereby span across interstices of the tubular scaffold 12 may prevent tissue ingrowth along their respective surfaces and interstices therebetween. The covering 26 may prevent the tissue from growing into the lumen of stent 10.

However, it can be appreciated that tissue may be permitted to grow around, between, through, within, etc. portions of the stent 10 in which the covering 26 is not present. For example, it can be appreciated that tissue may be permitted to grow around, between, through, within the filaments 30 of the tissue ingrowth scaffold 28.

Figure 5:
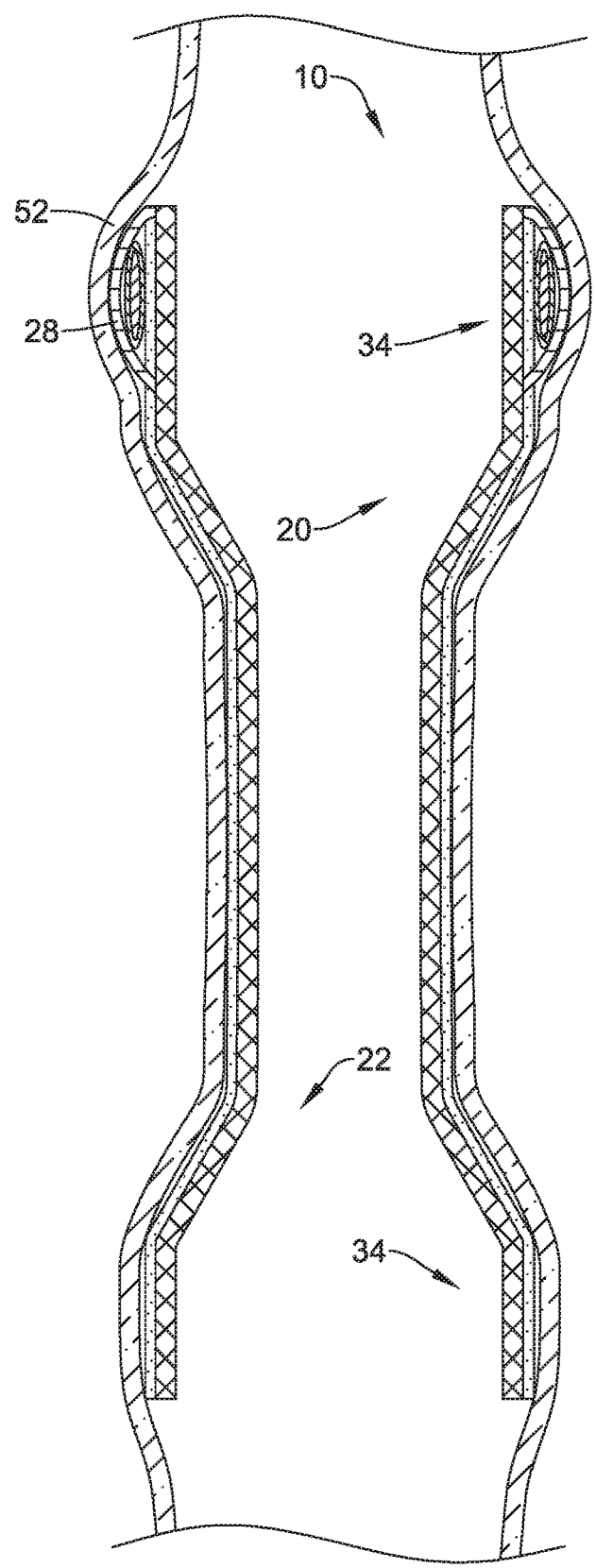
FIG. 5 illustrates an example stent positioned within a body lumen.
Figure 6:
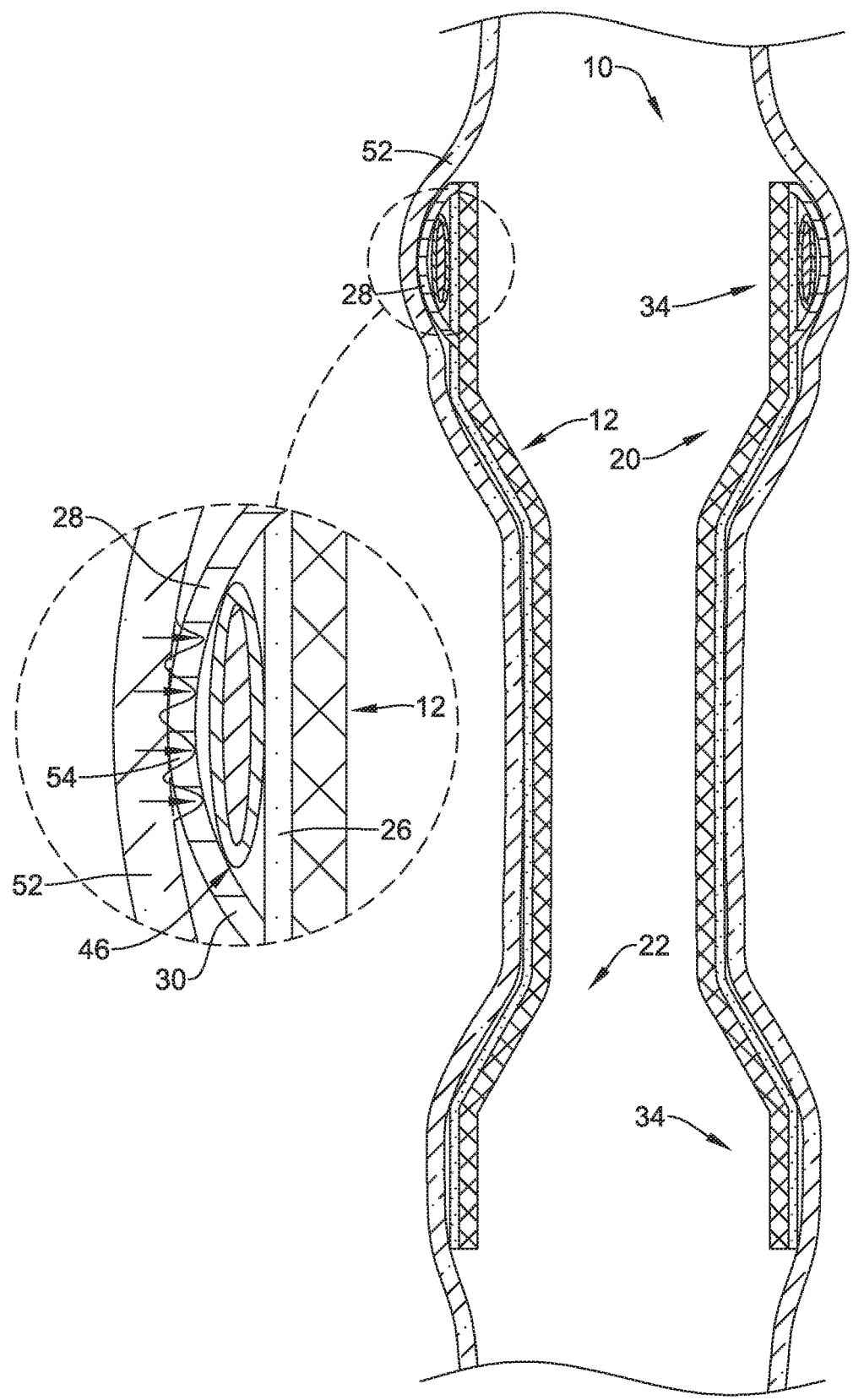
FIG. 6 illustrates a portion of the example stent shown in FIG. 5 positioned within a body lumen.
Figure 7:
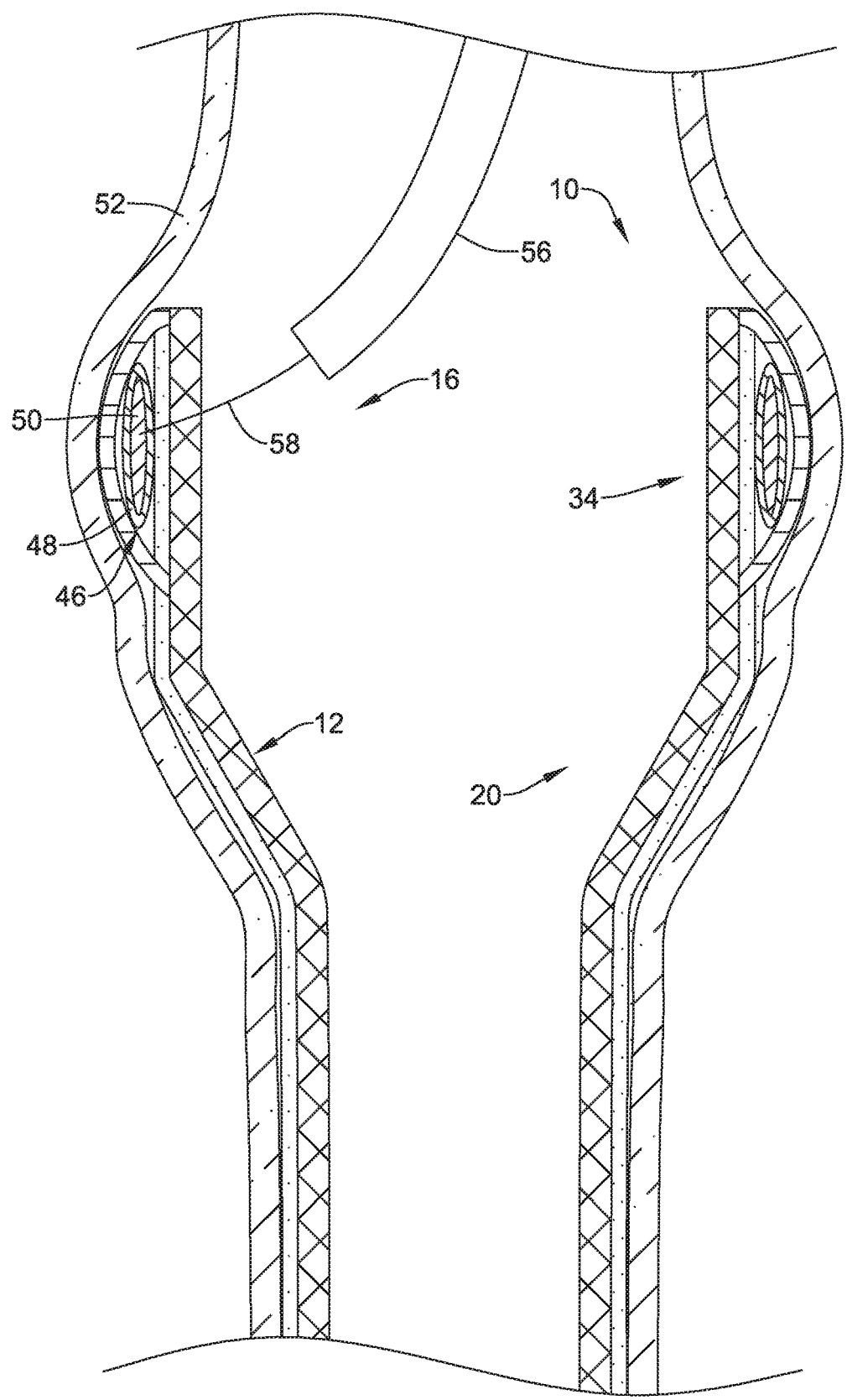
FIG. 7 illustrates a portion of the example stent shown in FIG. 5 positioned within a body lumen.
Figure 9:
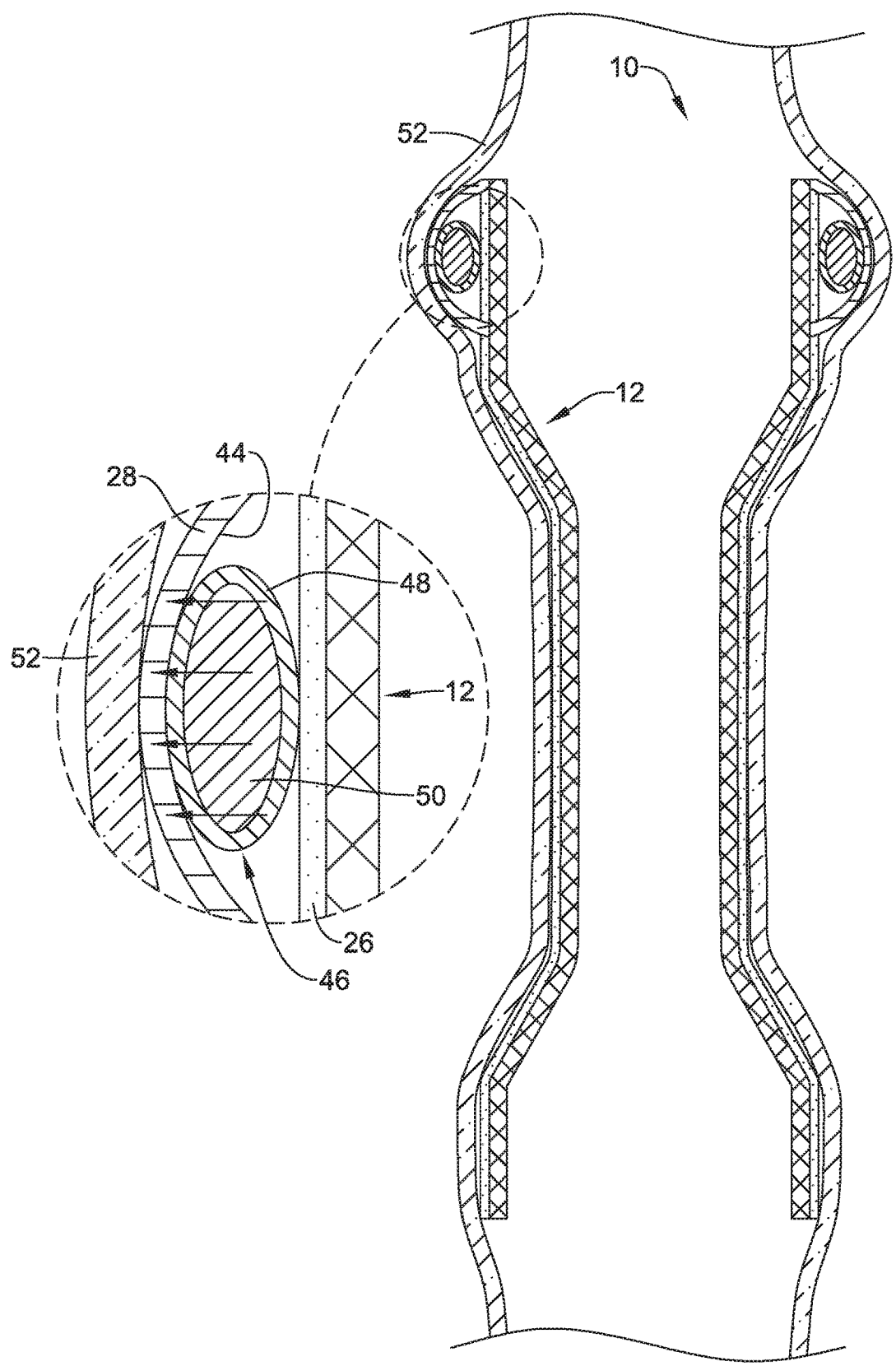
FIG. 9 illustrates a portion of the example stent shown in FIG. 5 positioned within a body lumen.
Figure 10:
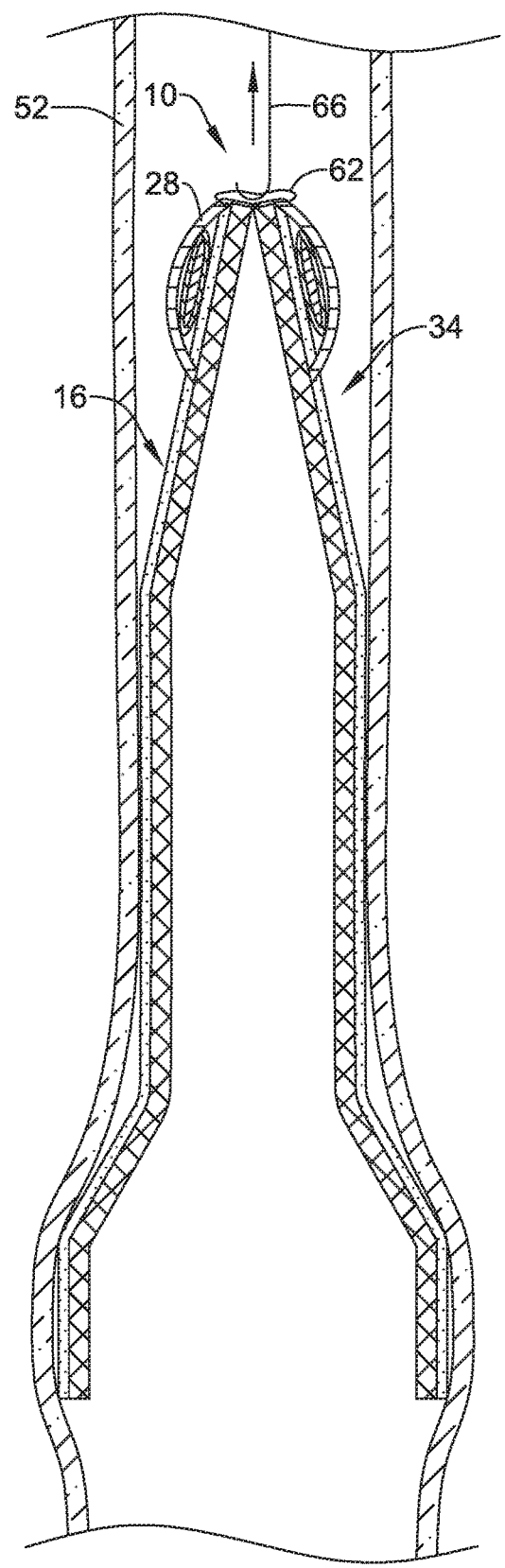
FIG. 10 illustrates the example stent shown in FIG. 5 being removed from a body lumen.

FIGS. 5-6 illustrate the example stent 10 undergoing a hyperplastic response while FIGS. 7 and 9-10 illustrate the removal of stent 10 via expansion of an expandable member to free the stent 10 from the ingrown tissue anchoring the stent 10.

FIGS. 5-6 illustrate the example stent undergoing a hyperplastic response of tissue within an example body lumen subsequent to implantation of the stent 10 (or any example stent embodiment described herein) within a body lumen 52. FIG. 5 shows the stent 10 deployed in body lumen 52. As illustrated, upon initial deployment in the body lumen 52, the end portion 34 of the first flared region 20 and the end portion 34 of the second flared region 22 may apply a radially outward force upon the inner surface of the body lumen 52 as the tubular framework 12 of the stent 10 expands to an expanded state in the body lumen 52. This radially outward force exerted on the inner surface of body lumen 52 may provide a temporary resistance to migration of the stent 10 within the body lumen 52.

Additionally, FIG. 5 illustrates that the tissue ingrowth scaffold 28 may contact the tissue on the inner surface of body lumen 52. The engagement of the tissue ingrowth scaffold 28 with the tissue along the inner surface of the body lumen 52 may provide a seal that permits food or other material to travel through the lumen of the stent 10 and, additionally, may prevent the food from traveling along the exterior of the stent 10 and along the inner surface of the body lumen 52. Additionally, it can be appreciated from the above discussion that the tissue ingrowth scaffold 28 may engage the tissue on the inner surface of the body lumen 52 circumferentially along the inner surface of the body lumen 52.

Engagement of the tissue ingrowth scaffold 28 may stimulate the onset of a hyperplastic response along the tissue ingrowth scaffold 28. The hyperplastic response may result in tissue from the body lumen 52 to grow through the interstices of the tissue ingrowth scaffold 28. For example, FIG. 6 illustrates tissue 54 extending through the interstices of the filaments 30 along the tissue ingrowth scaffold 28 of the stent 10. As discussed above, the tissue ingrowth scaffold 28 (including the filaments 30) may be uncovered, and therefore, may permit the radially inward growth of tissue through the interstices of the tissue ingrowth scaffold 28. However, the presence of the covering 26 radially inward of the tissue ingrowth scaffold 28 may prevent the growth of tissue through the tubular framework 12 into the lumen of the stent 10. FIG. 6 further illustrates that the tissue 54 may grow in a direction toward the tubular framework 12 (as depicted by the arrows in FIG. 6) and into the filaments 30 of the tissue ingrowth scaffold 28. It can be appreciated that the growth of tissue through the interstices of the tissue ingrowth scaffold 28 may anchor the stent 10 along the body lumen 52, thereby limiting or preventing the stent 10 from being dislodged due to peristaltic or other forces acting upon it.

In some instances, it may be desirable to remove the stent 10 subsequent to the tissue in-growth through interstices of the tissue ingrowth scaffold 28. However, the tissue-ingrowth may hinder removal and/or cause undesirable trauma to the body lumen. As discussed above, FIGS. 7 and 9-10 illustrate an example methodology for removing and retrieving an example stent 10 (or any other devices disclosed herein) from a body lumen while reducing the amount of trauma to the body lumen. Example stent 10 shown in FIGS. 7 and 9-10 may depict the stent 10 or stent 110 illustrated and described above with respect to FIGS. 1-6. Further, it is contemplated that the methodology described herein with respect to FIGS. 7 and 9-10 may be used to retrieve and/or remove stent 10, stent 110, stent 210 or any other devices disclosed herein.

It can be appreciated that one method to remove a stent which has been anchored via a hyperplastic response (e.g., tissue ingrowth) may be to reverse the ingrowth of tissue. In other words, one technique to free a stent that is anchored to tissue along an inner surface of a body lumen (such as stent 10, stent 110 or any other stent described herein) may include pushing the tissue radially outward with sufficient force such that the tissue recedes back through the stent filaments, thereby freeing the filaments from the tissue.

FIG. 7 illustrates an example first step in removing the stent 10 from an example body lumen 52 via forcing the ingrown tissue to recede back through the filaments 30 of the tissue ingrowth scaffold 28. As discussed above, the expandable member 46 may include an expandable material 50 encapsulated in a sleeve member 48. In some examples, the expandable material 50 may expand when it comes into contact with a substance that causes (e.g. activates, stimulates, energizes, triggers, elicits, etc.) the expandable material 50 to shift from a first, unexpanded volume to a second, expanded volume greater than the first volume. For example, the expandable material 50 may be a particular material (e.g., superabsorbent polymer) that absorbs a particular media (e.g., water, saline, etc.) and expands volumetrically in response to that absorption. It is contemplated that a variety of different expandable materials and activating solutions may be utilized to achieve the volumetric expansion described above. Some examples of the expandable materials and activating solutions and/or stimuli are disclosed herein, however, other types of expandable materials and activating solutions and/or stimuli are contemplated.

It can be appreciated that the sleeve 48 surrounding the expandable material 50 may need to be constructed from a material which is flexible enough to expand in response to the expansion of the expandable material 50 and, yet, strong enough to contain the expandable material 50 without rupturing. In other words, the sleeve 48 needs to be strong enough to prevent material from pre-maturely leaking prior to the desired expansion of the expandable material 50.

FIG. 7 illustrates one example methodology for activating (e.g., contacting, engaging, etc.) the expandable material 50 by injecting a liquid through the sleeve 48 or piercing the sleeve 48 to permit surrounding bodily fluid to contact the expandable material 50. FIG. 7 shows a delivery catheter 56 having been advanced and positioned adjacent to the first end 16 of the stent 10. FIG. 7 further illustrates an injection needle 58 which has been extended through a lumen of the delivery catheter 56 and advanced such that the distal end of the needle 58 penetrates through the tubular framework 12, the covering 26, and the sleeve 48. After penetrating through the tubular framework 12, the covering 26, and the sleeve 48, the distal end of the needle 58 may be in contact with the expandable material 50, whereby a liquid may be injected through the needle such that the liquid contacts the expandable material 50. Alternatively, the needle 58, or penetrator, may be utilized to pierce the sleeve 48 to permit surrounding bodily fluid to contact the expandable material 50. It is further contemplated that a needle 58, a penetrator, (or similar device) may be inserted directly through the skin of a patient from a location adjacent the expandable member 46.

It can be appreciated that the expandable member 46 may be designed such that other methods may be utilized to cause expansion of the expandable material 50. For example, the sleeve 48 may be constructed from biodegradable and/or bioabsorbable material and the expandable member 46 may be designed from material that expands upon contact with the bodily fluids present within the body lumen 52. Accordingly, it can be appreciated that as the biodegradable material degrades, the expandable material 50 may be exposed to and expand in response to contact with the bodily fluids in the body lumen 52. Further, the biodegradable sleeve 48 may be designed to biodegrade over a time period, thereby exposing the expandable material to bodily fluids (e.g., blood, mucus, etc.) after a predetermined delay. It is further contemplated that biodegradation described above may be trigger by a specific stimuli. For example, a change in the pH of an administered solution may be utilized to trigger the biodegradation of the sleeve 48.

Additionally, it is contemplated that the sleeve 48 may be formed from a porous material. The porous material may be designed such that bodily fluids may penetrate (e.g., diffuse, infiltrate, etc.) through the sleeve 48 at a rate dictated by the specific porosity of the material used to construct the sleeve 48. In other words, the sleeve 48 may be designed to permit bodily fluid to pass therethrough, thereby permitting the expandable material 50 to contact the bodily fluid at a given rate over a particular time period. Further, the expandable material 50 may be designed to expand after a predetermined amount of fluid has penetrated through the porous sleeve 48 and contacted the expandable material 50.

Figure 8:
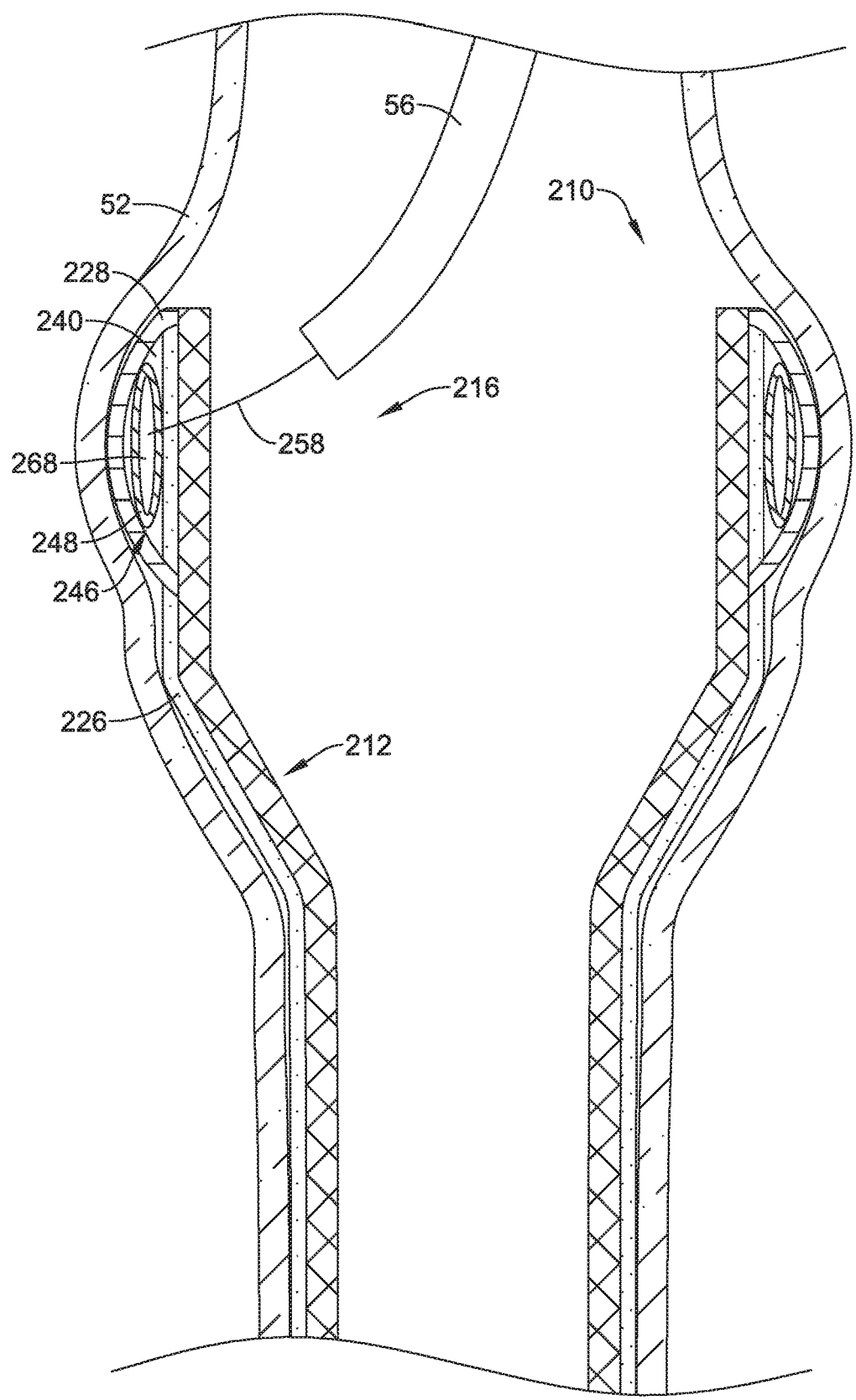
FIG. 8 illustrates another example stent.

FIG. 8 illustrates another example stent 210. The stent 210 may be similar in form and function similarly to other stents disclosed herein. For example, the stent 210 may include a tubular framework 212 having a covering 226 disposed thereon. Additionally, the stent 210 may include a tissue ingrowth scaffold 228 positioned radially outward of the tubular framework 212 and covering 226. Further, an expansion cavity 240 may be defined between the tissue ingrowth scaffold 228 and the tubular framework 212 (and covering 226). As shown in FIG. 8, an expandable member 246 may be positioned within the expansion cavity 240. However, it is contemplated that the expandable member 246 may be inflatable. In other words, as shown in FIG. 8, the expandable member 246 may include an inflatable sleeve 248 which defines an inflation chamber 268. The inflation chamber 268 would be free of expandable material as described above with respect to stent 10, 110. However, the inflation chamber 268 of stent 210 may be filled with a gel, a liquid, a gas or any other fluid (or combinations thereof) which could be utilized to expand the inflatable sleeve 248.

FIG. 8 further illustrates a delivery catheter 56 having been advanced and positioned adjacent to the first end 216 of the stent 210. FIG. 8 further illustrates an inflation device 258 which has been extended through a lumen of the delivery catheter 56 and advanced such that the distal end of the device 258 engages and/or penetrates the expandable sleeve 248. A variety of design configurations are contemplated to inject inflation media into the inflation chamber 268. For example, a needle may be used to penetrate sleeve 248, whereby the inflation media could be inserted into the inflation chamber 268. Additionally, it is contemplated that the sleeve 248 may include an inflation valve designed to couple with the distal end of the inflation device 258. After injection of the inflation media, the inflation device 258 and delivery catheter 56 may be retracted out of the patient.

FIG. 9 shows the stent 10 positioned in the body lumen 52 as described above. However, the detailed view of FIG. 9 further illustrates the expansion of the expandable member 46 via the radially outward expansion of the expandable material 50. As described above, it can be appreciated that after the expandable material 50 has been activated, such as exposed to a stimuli, inflated, or contacted by a material (e.g., liquid, etc.) that causes the volumetric expansion of the expandable material 50, the expandable material 50 may expand radially outward, axially or both radially outward and axially. In other words, the expandable material 50 may expand from the tubular framework 12 (including covering 26) toward the tissue grown into tissue ingrowth scaffold 28 (via the hyperplastic response, as described above).

In some instances the stent 10 may be configured to bias the direction in which the expandable member 46 expands. For example, the detailed view of FIG. 9 illustrates that stent 10 may be designed to bias the expandable member 46 to expand radially outward (as shown by the arrows in the detailed view of FIG. 9). It can be appreciated that in order to bias the expandable member 46 to expand radially outward (e.g., from the tubular framework 12 toward the tissue ingrowth scaffold 28), the tubular framework 12 may be designed to have a greater resistance to radially inward compression than the tissue ingrowth scaffold 28 has to radial outward expansion. In other words, as the expandable material 50 radially expands, it may exert a uniform force in all directions, however, because the tubular framework 12 may be designed to have a greater resistance to inward compression than the tissue ingrowth scaffold 28 has to outward stretching, the expandable member 46 may expand in the direction of least resistance and, therefore, push radially outward on the inner surface 44 of tissue ingrowth scaffold 28 and any tissue ingrown into tissue ingrowth scaffold 28. Further, it can be appreciated that as the expandable member 46 pushes against the inner surface 44 of the tissue ingrowth scaffold 28, it may push against the tissue 54 (not shown in FIG. 9, but shown in FIG. 6) which has grown into the tissue ingrowth scaffold 28 (via a hyperplastic response as described above). This outward force exerted on the tissue by the expandable member 46 may cause the tissue to recede back through the interstices of the tissue ingrowth scaffold 28, thereby reducing tissue trauma upon removal of the stent 10 and/or freeing the stent 10 from the body lumen. It is contemplated that any of the examples of expandable members disclosed herein may function in a similar manner as that described above.

It can be appreciated that the amount of force generated by the expandable member 46 may be proportional to the amount of expandable material 50 utilized in the design of stent 10. In other words, the more expandable material 50 that is positioned within the expandable member 46 will generate a greater volumetric expansion and thus greater radially outward force as compared to an equivalent stent design having a lesser amount of expandable material 50. Similarly, it can be appreciated the tissue ingrowth scaffold 28 may be configured to limit the amount of radial outward expansion generated by the expandable member 46. For example, the tissue ingrowth member 28 may be designed such that it has a limited radial expansion. In other words, the tissue ingrowth member 28 may be designed to expand up to a threshold diameter, at which point it will not expand any further. This threshold diameter may be correlated to a maximum expansion force generated by the expandable member 46.

As described above, FIG. 9 illustrates stent 10 after the expandable member 46 has been allowed to exert an outward radial force along the inner surface 44 of the tissue ingrowth scaffold 28 of the stent 10. As can appreciated from FIG. 9, the tissue 54 present in FIG. 6 has effectively died off due to the outward radial force placed upon it by the expandable member 46. Tissue death due to an outward radially force placed thereupon may be referred to as "pressure necrosis." As discussed above, because the expandable member 46 has reduced the amount of tissue 54 extending through the tissue ingrowth scaffold 28, the tissue 54 no longer attaches the stent 10 to the inner surface of body lumen 52 with as much force as when the tissue 54 is fully ingrown into the tissue ingrowth scaffold 28. Accordingly, this reduced attachment force translates into a lower force which is necessary to remove stent 10 from the body lumen 52, and thus less trauma to the body lumen 52.

FIG. 10 illustrates an example step in removing stent 10 from the body lumen 52. Removal of the stent 10 may be performed once tissue that has grown into the tissue ingrowth scaffold 28 of the stent 10 has sufficiently receded. For example, removal of stent 10 may be performed approximately 7-14 days after expansion of the expandable member 46. In some instances, removal of stent 10 may be performed within 1 week or less, within 2 weeks or less, or within 3 weeks or less after expansion of the expandable member 46. Specifically, FIG. 10 illustrates that a clinician may utilize a retrieval device 66 (e.g., hook, forceps, etc.) to grasp or hook a retrieval suture 62 extending circumferentially around the end of stent 10. When pulled proximally, the retrieval suture 62 may collapse the first end 16 of stent 10 to facilitate withdrawal of the stent 10. The force exerted by the retrieval device 66 may be sufficient to remove the stent 10 from the inner surface of the body lumen 11 without damaging the inner surface of the body lumen 11.

Figure 11:
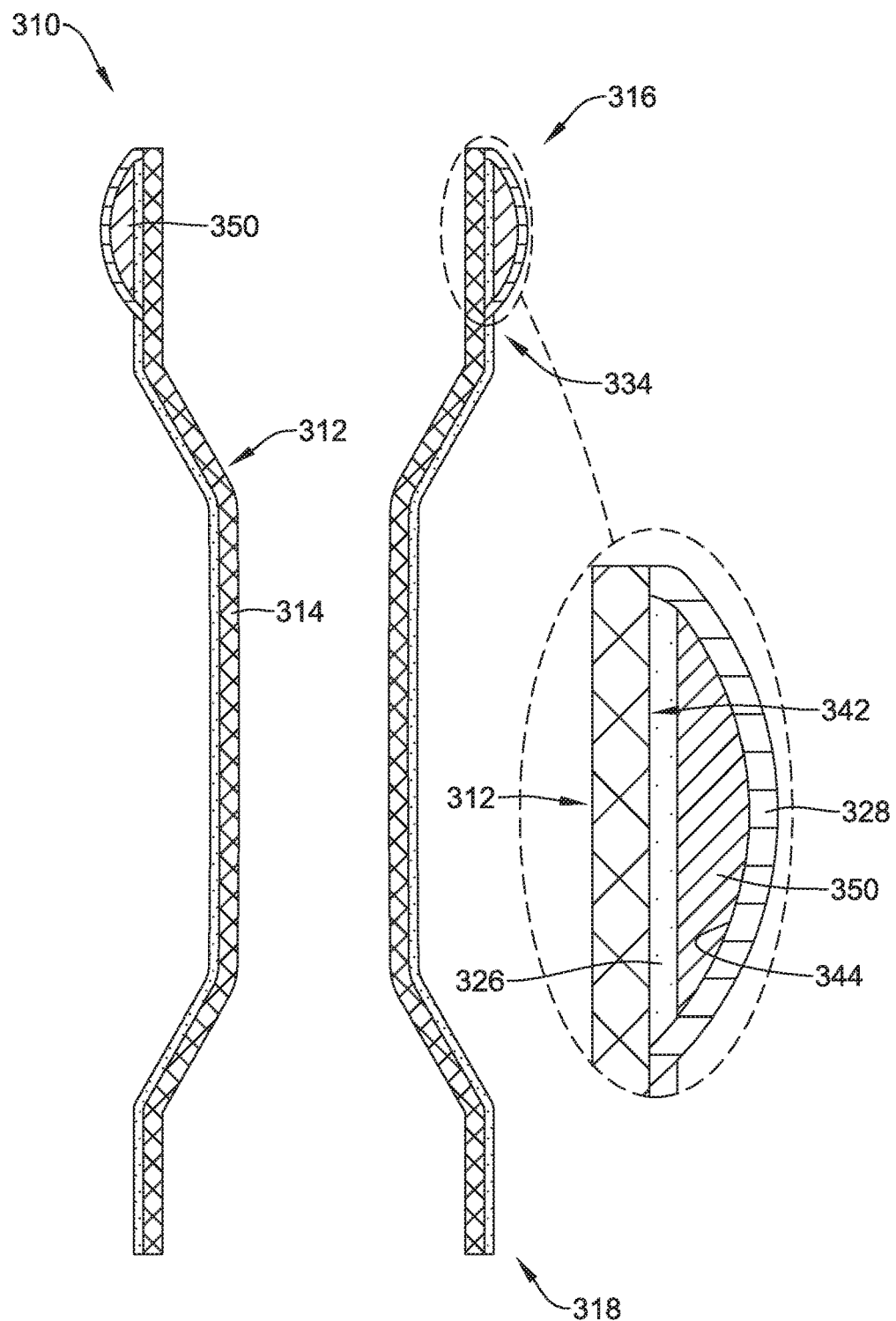
FIG. 11 illustrates another example stent.

FIGS. 11-14 illustrate another example stent 310. Stent 310 and FIGS. 11-14 may be similar to the stent 10 and FIGS. 5-7 and 9. For example, FIG. 11 illustrates stent 310 including a tubular framework 312 having a covering 326 disposed along a portion thererof. Similarly to that described above, the covering 326 may prevent tissue from growing through the filaments 314 of the tubular framework 312 and into the lumen of the tubular framework 312. Further, FIG. 11 illustrates that the stent 310 may include a tissue ingrowth scaffold 328 similar to the tissue ingrowth scaffold 28 described above. Tissue ingrowth scaffold 328 may be positioned radially outward of the tubular framework 312 and covering 326, defining an expansion cavity therebetween. Additionally, the detailed view of FIG. 11 shows that the stent 310 may simply include an expandable material 350 that is disposed within the expansion cavity defined between the tubular framework 312 and the tissue ingrowth scaffold 328. The expandable material 350 may include a superabsorbent material (e.g., superabsorbent foam, superabsorbent beads, etc.). In some examples, the superabsorbent material may be formed into small beads which are encapsulated in a magnetically responsive material, an electroactive polymer, an ultrasound responsive material, or other similar material. When activated by a specific stimuli (e.g., magnetic waves, electromagnetic field, electroactive waves, ultrasound waves, etc.), the beads may break apart, thereby exposing the superabsorbent material to surrounding bodily fluids. As discussed above, absorption of the fluid by the superabsorbent material may result in the expansion of the superabsorbent material. Further, in some examples the expandable material may be coupled to either the outer surface 342 of the tubular framework 312, the covering 326 and/or the inner surface 344 of the tissue ingrowth scaffold 328.

Figure 12:
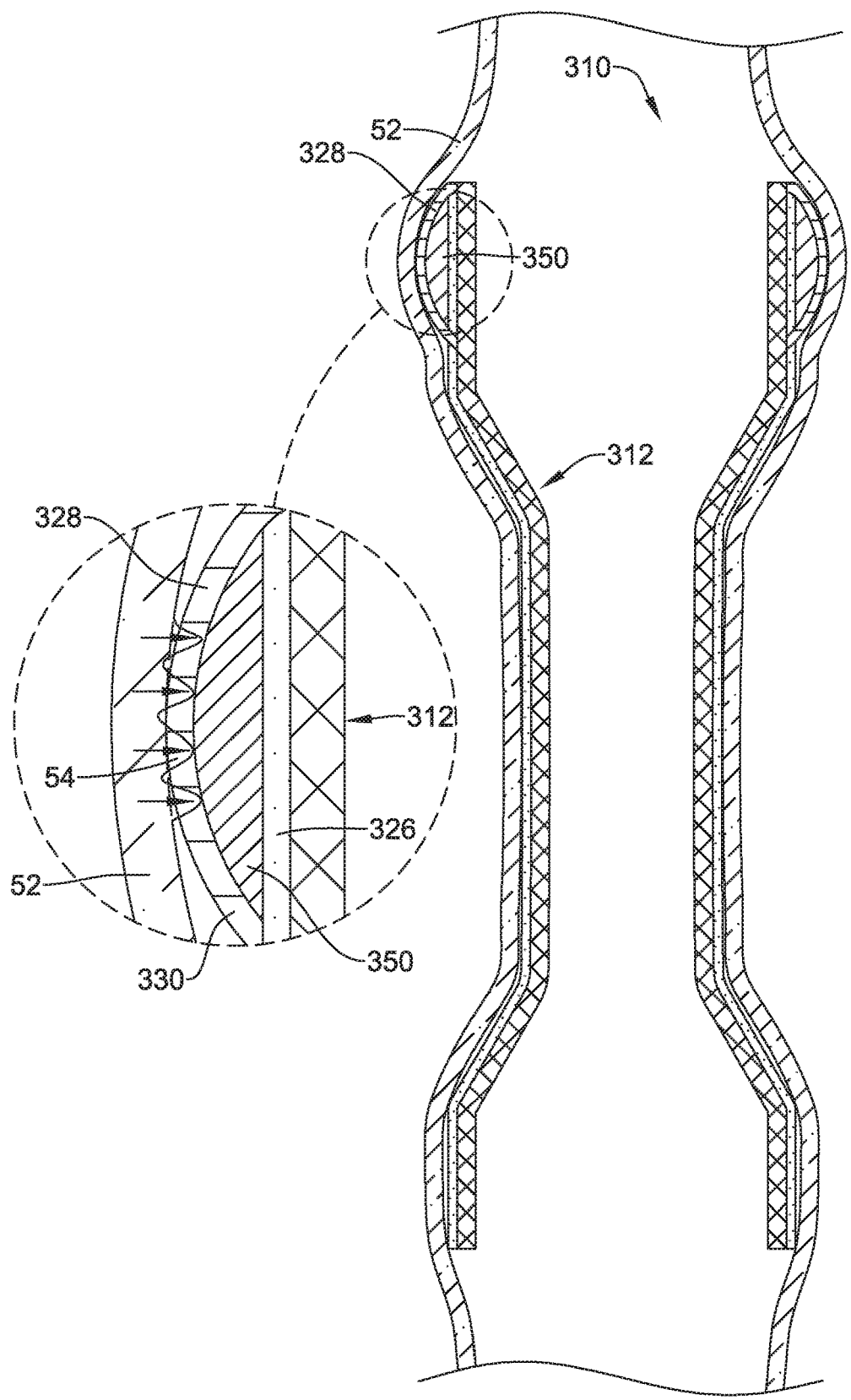
FIG. 12 illustrates a portion of the example stent shown in FIG. 11 positioned within a body lumen.

Similar to FIG. 6, FIG. 12 illustrates the stent 310 undergoing a hyperplastic response. For example, FIG. 12 illustrates tissue 54 extending through the interstices of the filaments 330 along the tissue ingrowth scaffold 328 of the stent 310. As discussed above, the tissue ingrowth scaffold 328 (including the filaments 330) are uncovered, and therefore, permit the radially inward growth of tissue through the interstices of the tissue ingrowth scaffold 328. FIG. 12 further illustrates that the tissue 54 may grow into the tissue ingrowth region 328 toward the expandable material 350 and the covering 326 (as depicted by the arrows in FIG. 12). It can be appreciated that the growth of tissue through the interstices of the tissue ingrowth scaffold 328 may anchor the stent 310 along the body lumen 52, thereby limiting or preventing the stent 310 from being dislodged due to peristaltic or other forces acting upon it.

Figure 13:
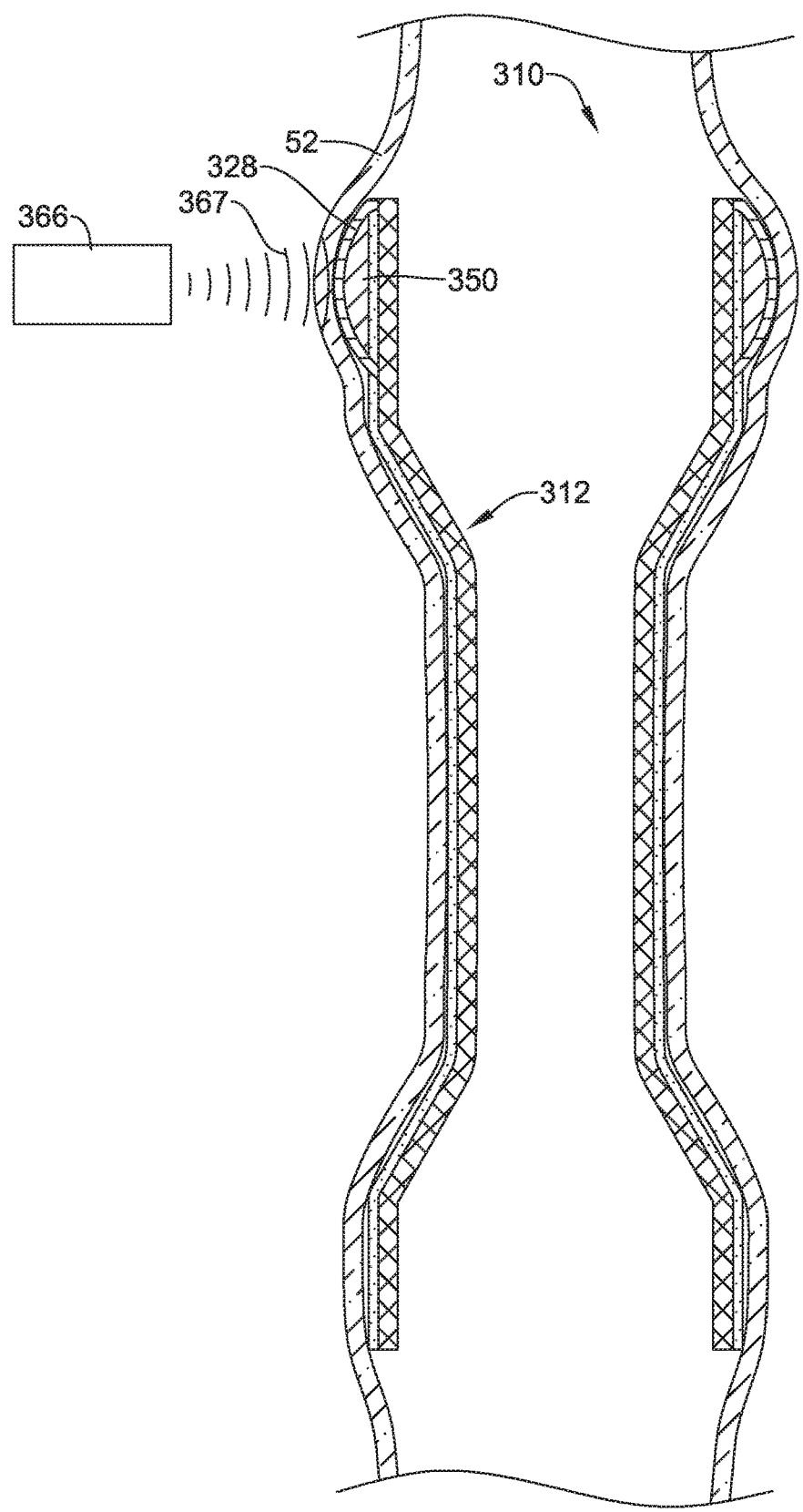
FIG. 13 illustrates a portion of the example stent shown in FIG. 11 positioned within a body lumen.

FIG. 13 illustrates one example methodology to activate the expandable material 350 described above. FIG. 13 illustrates that in some examples, a source 366 (which may be positioned inside or outside of a patient's body) may be utilized to cause the expandable material 350 to expand. In some examples, the source 366 may emit an activation "signal" 367 or stimuli which activates or stimulates the expandable material 350, as described above. The signal 367 may include many different forms, some of which are described below.

For example, the source 366 may include an ultrasound device which is designed to emit ultrasound waves 367. The ultrasound waves 367 may pass through a patient's body (including the body lumen 52), through the tissue ingrowth scaffold 328 and contact the expandable material 350. The expandable material 350 may be designed to expand in response to the ultrasound waves 367.

In another example, the source 366 may emit magnetic waves. The magnetic waves 367 may pass through the patient's body (including the body lumen 52), through the tissue ingrowth scaffold 328 and contact the expandable material 350. The expandable material 350 may be designed to expand in response to the magnetic waves.

In yet other examples, the source 366 may emit electroactive signals. The electroactive signals 367 may pass through the patient's body (including the body lumen 52), through the tissue ingrowth scaffold 328 and contact the expandable material 350. The expandable material 350 may include an electroactive polymer which is designed to expand in response to the electroactive signals.

Additionally, it is contemplated that in some examples the source 366 may be utilized to initiate the biodegradation of the sleeve 48 described above with respect to stent 10. For example, a source 366 positioned outside a patient's body may be used to initiate the biodegradation of the sleeve 48 surrounding the expandable material 50. This may permit a clinician to precisely control the rate and timing in which the expandable material 50 may be exposed to bodily fluids which may cause its expansion (and, ultimately, the release of the stent 10 from a body lumen).

Figure 14:
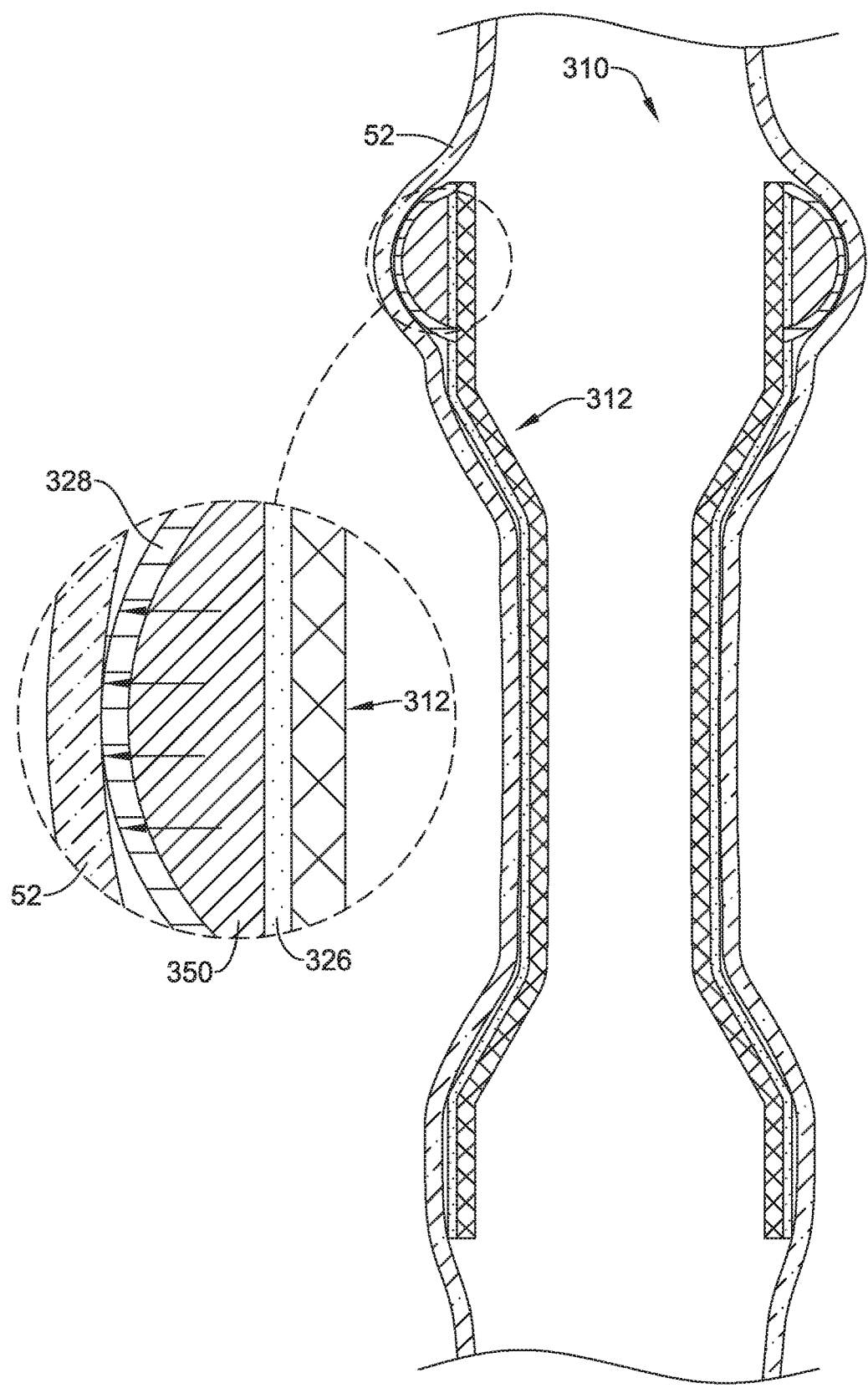
FIG. 14 illustrates a portion of the example stent shown in FIG. 11 including expansion of an expandable material.

Similar to FIG. 9, the detailed view of FIG. 14 illustrates the radially outward expansion of the expandable material 350. As described above with respect to FIG. 9, it can be appreciated that after the expandable material 350 is activated by a stimulus that causes the volumetric expansion of the expandable material 350, the expandable material 350 may expand radially outward. In other words, FIG. 14 illustrates the expandable material 350 may expand from the tubular framework 312 (including covering 326) toward the tissue which has grown into tissue ingrowth scaffold 328 (via a hyperplastic response, as described above). Similarly to FIG. 9, the detailed view of FIG. 14 illustrates that stent 310 may be designed to bias the expandable material 350 to expand radially outward (as shown by the arrows in the detailed view of FIG. 14) to exert a radially outward force on the tissue which has grown into the tissue ingrowth scaffold 328, thereby reducing tissue trauma upon removal of the stent 310 and/or releasing the stent 310 from the body lumen as described above.

The materials that can be used for the various components of stent 10 and stent 310 (and/or other stents disclosed herein) and the various medical devices disclosed herein may include those commonly associated with medical devices. For simplicity purposes, the following discussion makes reference to stent 10 and stent 310 and other components of stent 10 and stent 310. However, this is not intended to limit the devices and methods described herein, as the discussion may be applied to other similar medical devices disclosed herein.

Stent 10, stent 110, stent 210 and stent 310 and other components of stent 10, stent 110, stent 210 and stent 310 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of stent 10, stent 110, stent 210 and stent 310 and other components of stent 10, stent 110, stent 210 and stent 310 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of stent 10, stent 110, stent 210 and stent 310 in determining their locations. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of stent 10, stent 110, stent 210 and stent 310 to achieve the same result.

In some embodiments, a degree of Magnetic Resonance Imaging (MRI) compatibility is imparted into stent 10, stent 110, stent 210 and stent 310. For example, stent 10, stent 110, stent 210 and stent 310 and other components of stent 10, stent 110, stent 210 and stent 310, or portions thereof, may be made of a material that does not substantially distort the image and create substantial artifacts (e.g., gaps in the image). Stent 10, stent 110, stent 210 and stent 310 and other components of stent 10, stent 110, stent 210 and stent 310 or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A stent, comprising:
    a tubular framework, the tubular framework including an inner surface, an outer surface and a lumen extending therethrough;
    a tissue ingrowth scaffold extending along a portion of the outer surface of the tubular framework, wherein the tissue ingrowth scaffold is spaced radially away from the outer surface of the tubular framework to define an expansion cavity therebetween, and wherein the tissue ingrowth scaffold permits tissue ingrowth along a portion thereof;
    a covering disposed along a portion of the tubular framework, wherein the covering is configured to prevent tissue from growing into the lumen of the tubular framework; and
    an expandable member positioned within at least a portion of the expansion cavity.

2. The stent of claim 1, wherein the expandable member is configured to expand radially outward toward an inner surface of the tissue ingrowth scaffold.

3. The stent of claim 1, wherein the expandable member is configured to exert a radially outward expansion force on the tissue ingrowth scaffold such that an outer surface of the tissue ingrowth scaffold shifts radially outward from a first position to a second position.

4. The stent of claim 1, wherein the expandable member is configured to exert a radially outward force upon the tissue ingrowth scaffold causing tissue ingrowth to recede.

5. The stent of claim 1, wherein the expandable member extends circumferentially around the outer surface of the tubular framework.

6. The stent of claim 1, wherein the expandable member includes an expandable sleeve and an expandable material positioned within a void of the expandable sleeve.

7. The stent of claim 6, wherein the expandable material is configured to expand when exposed to an external stimuli.

8. The stent of claim 7, wherein the external stimuli is a liquid.

9. The stent of claim 6, wherein the expandable sleeve is configured to dissolve over a time period to expose the expandable material.

10. The stent of claim 1, wherein the expandable member includes an inflatable sleeve, and wherein the inflatable sleeve is configured to shift from a first unexpanded configuration to a second expanded configuration when inflated.

11. The stent of claim 1, wherein the tissue ingrowth scaffold extends along the outer surface of the tubular framework from an end of the tubular framework, and wherein the scaffold folds back on the tubular framework to form the expansion cavity.

12. The stent of claim 1, wherein the tissue ingrowth scaffold includes a wire mesh having one or more apertures configured to permit tissue ingrowth therethrough.

13. A stent, comprising:
- a tubular framework having a first end and a second end opposite the first end, the tubular framework including an inner surface, an outer surface and a lumen extending therethrough;
- a tissue ingrowth scaffold extending along a portion of the outer surface of the tubular framework, wherein the tissue ingrowth scaffold is spaced radially away from the outer surface of the tubular framework to define an expansion cavity therebetween, and wherein the tissue ingrowth scaffold permits tissue ingrowth along a portion thereof;
- a covering disposed along the tubular framework, wherein the covering is configured to prevent tissue from growing into the lumen of the tubular framework between the first end and the second end; and
- an expandable member positioned within at least a portion of the expansion cavity, the expandable member configured to radially expand from a first nominal state to an expanded state when subjected to an external stimuli, wherein the expandable member is configured to exert a radially outward force upon the tissue ingrowth scaffold in the expanded state to cause tissue ingrowth within the tissue ingrowth scaffold to recede.

14. The stent of claim 13, wherein the expandable member is configured to expand radially outward toward an inner surface of the tissue ingrowth scaffold.

15. The stent of claim 13, wherein the expandable member extends circumferentially around the outer surface of the tubular framework.

16. The stent of claim 13, wherein the expandable member includes an expandable sleeve and an expandable material positioned within a void of the expandable sleeve.

17. The stent of claim 16, wherein the external stimuli is a liquid.

18. The stent of claim 13, wherein the tissue ingrowth scaffold includes a wire mesh having one or more apertures configured to permit tissue ingrowth therethrough.

19. A stent, comprising:
- a tubular framework formed of one or more interwoven filaments, the tubular framework including an inner surface, an outer surface and a lumen extending therethrough;
- a tissue ingrowth scaffold extending along a portion of the outer surface of the tubular framework, wherein the tissue ingrowth scaffold is spaced radially outward away from the outer surface of the tubular framework to define an expansion cavity therebetween, and wherein the tissue ingrowth scaffold permits tissue ingrowth along a portion thereof;
- a covering disposed along a portion of the tubular framework, wherein the covering is configured to prevent tissue from growing into the lumen of the tubular framework; and
- an expandable polymeric member positioned within at least a portion of the expansion cavity;
- wherein the expandable polymeric member is configured to radially expand from a first nominal state to an expanded state when subjected to an external stimuli, wherein the expandable polymeric member is configured to exert a radially outward force upon the tissue ingrowth scaffold in the expanded state to cause tissue ingrowth within the tissue ingrowth scaffold to recede.

* * * * *